United States Patent [19]

Cornell

[11] 4,233,288
[45] Nov. 11, 1980

[54] GUM EMULSIFIED LIQUID PACKAGE FOR DELIVERING AND PRESERVING LIQUID CONTENT IN THE MOUTH

[76] Inventor: John A. Cornell, 32nd and Spring Garden Sts., Philadelphia, Pa. 19104

[21] Appl. No.: 19,639

[22] Filed: Mar. 12, 1979

[51] Int. Cl.³ .............................................. A61K 9/68
[52] U.S. Cl. .......................................... 424/48; 426/4; 426/5; 426/6; 424/52
[58] Field of Search ...................... 424/48; 426/4, 5, 6

[56] References Cited

U.S. PATENT DOCUMENTS

| | | | |
|---|---|---|---|
| 2,627,493 | 2/1953 | Merckel et al. | 424/48 |
| 3,085,048 | 4/1963 | Bush | 424/48 |
| 3,639,569 | 2/1972 | Medcalf | 424/48 |
| 3,992,519 | 11/1976 | Hofmann | 424/48 |
| 4,151,270 | 4/1979 | Ream | 424/48 |
| 4,154,814 | 5/1979 | Hand | 424/48 |

FOREIGN PATENT DOCUMENTS

| | | | |
|---|---|---|---|
| 2548367 | 5/1976 | Fed. Rep. of Germany | 424/48 |
| 2320083 | 3/1977 | France | 424/48 |

OTHER PUBLICATIONS

Handbook of Nonprescription Drugs, 5th Ed. (1977) Published by Am. Pharm. Assoc. Wash. D.C. pp. 249, 250, 259, 260, 262 & 263.

*Primary Examiner*—Douglas W. Robinson
*Attorney, Agent, or Firm*—Abraham A. Saffitz

[57] ABSTRACT

A composition containing critical proportions of 3 to 5 parts filler, 25 to 35 parts chewing gum base, gum chicle or SBR synthetic rubber, a minimum amount of emulsifier and from 40 to 62 parts of a water based emulsified phase. The emulsified water phase contains 3 to 6 parts sweetener and dissolved, inorganic mineral salts, such as sodium, potassium, calcium and magnesium chlorides and potassium phosphates, at a concentration of about 1% to 3% of the water phase, which is in the physiological range to ameliorate medical conditions such as xerostoma by controlling release of the dilute mineral salt solution during chewing thereof. When saliva is lacking, the liquid may contain dissolved salts higher than the physiological level, with or without 2 to 30 parts per million fluoride ions, so as to prevent demineralization of teeth. Under the direct supervision of a physician or dentist, the fluoride ions (NaF, $SnF_2$ or sodium fluorophosphate) may be increased to 500 to 1000 parts per million depending upon frequency of use. Other additives may be introduced to the water phase such as coating compositions for the teeth or medicants released to the digestive system. It is essential that the composition be packaged in a moisture-proof seal which can be accomplished with a foil coated wrapping inside a moisture barrier plastic, glass or metal container.

8 Claims, No Drawings

GUM EMULSIFIED LIQUID PACKAGE FOR DELIVERING AND PRESERVING LIQUID CONTENT IN THE MOUTH

BACKGROUND OF THE INVENTION

1. Field of the Invention

This invention lies in the field of chewing gums and particulary in the field of chewing gums containing a minor proportion of gum ingredients and a major proportion of a type of physiological salt solution at a concentration and in a condition of sterility to make it useful for treatment of xerostoma and other medical conditions where the flow of saliva is inadequate to provide proper oral hygiene.

2. Description of the Prior Art

A. Commericial Flavored Gums:

Liquid center gums have been just recently introduced into the commercial candy field, as shown in The New York Times report on Feb. 6, 1979 in the Advertising Section by Philip T. Dougherty. This section describes a new sugar free mint called "The Mint" and a chewing gum with a liquid center called "Spout". The liquid carries sweeteners and flavoring agents but these are used at very low proportions relative to the gum.

B. Special Mouth Treatment Gums:

Other commercial products for mouth treatment are available which contain ingredients which have a beneficial effect for only a limited time after introduction into the oral environment. These products are unsatisfactory because the ingredients and/or liquid are rapidly dissipated and lost which requires either massive initial doses or continued reapplication.

C. Gum As A Medication Vehicle:

Chewing gum as a vehicle for medication has been considered as an acceptable method of application. Generally a medicine in solid form may be used as a physical dispersion of a solid in the hydrophobic gum (see Finn and Jamison, 1967 Journal of the American Dental Association, Volume 74, page 987). Medicine may also be used as a coating on a gum in an excapsulated phase as shown in U.S. Pat. No. 3,962,463. Polymer-liquid composites have been proposed in U.S. Pat. No. 3,985,298. These have not gained acceptance.

D. Coated and Liquid Center Gum:

A small amount of liquid has been incorporated into the center of chewing gum, generally less than 5% of the weight, as shown in U.S. Pat. Nos. 810,210 and 3,857,963. Sugar coatings have also been used in gum to dispense aspirin and other digestive aids.

OBJECTS OF THE INVENTION

It is an object of the invention to increase the amount of physiological concentrations of mineral salts, including the chlorides of sodium, potassium, magnesium and calcium as well as potassium phosphate, to larger proportions whereby the long lasting qualities of the gum are enhanced to make it especially useful in the treatment of xerostoma and other conditions where the normal flow of saliva is impaired.

Other and further objects of the invention will become apparent from the following description, examples of preferred embodiment and claims.

SUMMARY OF THE INVENTION

The invention is directed to an emulsified water in gum composition, preferably in packaged stick form, comprising critical proportions of 3 to 5 parts filler, 25 to 35 parts gum base, a minimum amount of emulsifier and about 40 to 62 parts water in the water based emulsified phase containing up to 7% dissolved solids within the gum to provide thereby up to about 70% liquid. The water phase contains as an essential dissolved solids ingredient thereof dissolved inorganic mineral salts in a total concentration of about 1% to 3% of the water phase, these salts including sodium, potassium, magnesium and calcium chlorides and potassium phosphates with from 2 to 20 parts per million of fluoride ions as NaF which serves to prevent the demineralization of teeth. The mineral salt content or concentration may be adjusted to be isotonic, as is physiological salt solution, may be hypotonic, e.g., less than physiological salt concentration or only slightly higher. Where saliva is lacking, as, for example, in xerostoma, the liquid emulsified gum composition is especially useful because the mineral salt solution in diluted form is released slowly by chewing. The contact of this special gum with the teeth and peridontia serves to express the liquid, during chewing, in controlled amounts to continuously bath the teeth gums and interpoximal areas. Because of the slight abrasive action of the filler component, there is a cleansing action imparted during chewing to the teeth, interproximal areas and gum edges, thereby facilitating proper hygiene for patients suffering from xerostoma. In only about 15 minutes of chewing a very substantial quantity of physiological salt solution in sterile condition is brought mechanically into the saliva-starved oral cavity.

It is within the scope of the invention to include filming agents which can deposit on the surfaces of the teeth during chewing, such filming agents including those known to enhance remineralization and add resistance to demineralization during cariogenic attack.

It has been discovered that, with liquid content close to 50% or more, representing a water content of 40% and about 6% to 7% dissolved solids in the water phase, the release of liquid from the emulsified liquid phase is distinctively different from that in the usual emulsified gum having 5% to 10% liquid.

The release of liquid phase from the chewing gum is not linear at high liquid percentages, e.g., over 50%, as an initial burst of liquid occurs in the first few chews, presumably due to larger dispersed droplets. Since it is generally desirable to flush the entire oral cavity initially and then to have a slower rate of replacement for the liquid swallowed, this permits flushing with a small amount of dissolved antiseptic. In the normal individual, chewing enhances the flow of saliva from the ducts so that antiseptics or medicants are diluted and a lower concentration is available away from the surface of the gum and is ultimately swallowed. In the xerostoma patient, essentially no saliva may be present in the extreme case. Under these conditions the large amount of initial exudate from the gum is particularly desirable to wet the oral cavity. The lower rate of replacement is also desirable. The proper formulation of the components used for a specific medicant problem is more flexible in solving many of the delivery system problems. Use is made, in the present invention, of polymeric-hydrophilic materials such as carboxymethyl cellulose and fibrous cellulose to adjust the rate of dispersion of the medicant.

The achievement of a balance of hydrophobic properties in the chewing gum base, preferably gum chicle or gum gutta, with a major amount of hydrophilic liquid water containing phase, e.g., 50% to 70%, is surprising in view of the low quantity of hydrophobic gum. This permits a two stage release, first a fast release for immediate irrigation of the mouth followed by a second slower release. A medicant, such a pyridinium chloride, in concentrations of 0.1% to 1.0% may be included to assist lavage. Sweeteners and flavors which are non-cariogenic are preferred, such as xylitol, sorbitol, maltitol or sweetener substitutes such as saccharine or aspartane (as suggested in U.S. Pat. No. 3,982,023). As little as 4% of these non-cariogenic sweeteners may be used as compared to the 75% often used in commercial formulations which use glucose or sucrose, a 15 times reduction.

During about the first 3 minutes of chewing copious amounts of sterile salt solution are released in a first quick burst and then smaller amounts of liquid continue to be released at a slower rate so that a beneficial effect is achieved, e.g. providing artificial saliva during a 10 to 20 minute chewing period. If less than 1% mineral salts is present in the liquid phase, the same benefit is not achieved. If more than 3% mineral salts is present, the liquid irritates the mucous membranes. If the correct species of all salts is not present, the benefits of natural saliva are not achieved and the taste is objectionably altered. If coating of the teeth areas is desired, cephalin may be added. Slowing the rate of release of liquid from the gum is aided by incorporating up to 5% of very finely divided cellulose fibers. Glycerine and carboxymethyl cellulose (CMC) may be added to the liquid phase to increase viscosity, glycerine in amounts of from 0.25% to 2.5% and CMC in amounts of 0.2% to 2%. Carbohydrate sweeteners, especially sucrose, also increase viscosity to stabilize the liquid.

By keeping the dissolved solids to a total of 6 to 10 parts by weight and by using a critical dispersion stabilizer, a reproducible consistency of the liquid phase is achieved in the final product. The critical dispersion stabilizer is necessary to aid in mixing and emulsifying the liquid phase to the hydrophobic chewing gum base. The critical dispersion aid is a balanced hydrophilic lipophilic emulsifier with a value of 4 to 6 on the Hydrophilic Lipophilic Balance Scale (HLB Scale). Best results have been achieved with lipophilic emulsifiers having a value of 5 on the HLB Scale, such as Span 60, or a mixture of Atmul 84, Span 60 and Tween 60.

Critical Mixing Features for Special Gum Emulsified Liquid Composition

The procedure for producing the composition of the invention requires a careful order of addition of the components. The gum base, plasticizer and dispersion stabilizer are first added to a mixer, such as a Hobart Blender, and heated to melting at a temperature of about 60° up to about 70° C. The liquid phase is prepared by separately dissolving the salts, emulsifier, glycerine, cephalin, CMC and sweeteners. Cellulose fibers and the inorganic fillers, such as calcium phosphate, are then added to the liquid phase. This liquid phase, containing about 6% to 10% dissolved materials, is then slowly added to the mixing gum phase and blended at a temperature of at least 60° C. until a smooth, dough-like mass is produced. If the temperature is too low, excessive fibrous strands will form as the gum is mixed or dumped from the mixer onto a smooth surface. It is not desirable to heat above 70° C. which is high enough to sufficiently lower the viscosity to permit emulsification while keeping vaporization to a minimum. It was found that by holding back some ingredients, such as glycerine and flavoring, until the end of the mixing procedure, emulsification was aided. Completion of the emulsification is apparent in the disappearance of the liquid phase.

The gum is then rolled out to a flat form suitable for cutting, extruding or otherwise forming into the final shape.

It is extremely important to package the gum in a package with a moisture barrier to maintain the desired proportions. The product will not have the right properties if it is allowed to lose moisture.

Summary of Critical Proportions

In Table I below the critical proportions of the essential ingredients of the composition are set forth, these ingredients being mixed in accordance with the critical mixing procedure described above:

| | | |
|---|---|---|
| Gum Chicle or SBR Synthetic Rubber Gum | 25%–35% | |
| Non-Toxic Plasticizer | 3%–6% | |
| Sorbitol, Mannitol, Xylitol or Sucrose | 3%–6% | |
| Cellulose Filler (CMC Preferred) OR | 3%–5% | |
| Calcium Phosphate Inorganic Filler | 4%–5% | |
| Glycerine | 1%–3% | |
| Fluoride Ion (NaF, SnF$_2$ or Sodium Fluorophosphate) | 10–30 | ppm |
| | 500–1000 | ppm under direct professional supervision |
| Emulsifier - Value of 4–6 on HLB SCale | 0.1%–1% | |
| Solution Liquid Phase | 40%–61% | |
| Gum Phase | 60%–39% | |

To the above, flavoring agents and coloring agents may be added as desired.

Solution Liquid Phase

| | |
|---|---|
| Distilled Water | Makeup to 4000 ml |
| KCl | .4%–7% |
| NaCl | .8%–1.1% |
| MgCl$_2$ | .04%–.06% |
| CaCl$_2$ | .13%–.18% |
| K$_2$HPO$_4$ | .7%–1.0% |
| KH$_2$PO$_4$ | .2%–.6% |
| NaF | 2–20 ppm |
| Cephalin | .5%–1.5% |

DESCRIPTION OF THE PREFERRED EMBODIMENTS

Example 1 below sets forth a composition in accordance with the invention which illustrates the preferred gum base, namely SBR synthetic rubber gum base. The formula is a set out in Table II and Table III below. This formula is designated Formuly A for comparison with commercial gum stocks.

EXAMPLE 1

TABLE II

| Composition of Formula A: | |
|---|---|
| Synthetic Gum Base* | 27.5% |
| Coconut Oil Plasticizer | 4.6% |
| Liquid Solution (Table III) | 57.0% |
| Glycerine | 1.8% |
| Sorbitol | 3.4% |
| Dicalcium Phosphate Dihydrate | 4.6% |

TABLE II-continued

| | |
|---|---|
| Span 60** Emulsifier | 0.46% |
| Fungicide | 0.4% |
| methyl-p-hydroxy | 0.4% |
| Peppermint Oil | 0.45% |
| Mineral Salts Solution for Formula A: | |
| Distilled Water | Makeup to 4000 ml |
| KCl | 2.5 grams |
| NaCl | 3.46 grams |
| $MgCl_2$ | 0.235 grams |
| $CaCl_2$ | 0.665 grams |
| $K_2HPO_4$ | 3.2 grams |
| $KH_2PO_4$ | 1.3 grams |
| NaF | 2-20 ppm |
| Cephalin | 4.0 grams |

*Synthetic SBR rubber gum base supplied by L. A. Dreyfus Company under tradename LADCO
**Span 60 is Sorbitan monostearate supplied by I.C.I. Atlas Division, Wilmington, Delaware; BLH = 4.7

Although a large number of natural polymers may incorporate up to 90% liquid, few produce the gum properties needed for the feel and taste of chewing gum and most polymers lack cut-through resistance. Table IV below shows important gum properties of the invention as compared with typical chewing gums. On a cut-resistance scale on which an ideal gum is 5, most were barely acceptable at 3 or failed at 2, 1 or 0. Hardness varies from 0 to 10. Stickiness, resilience, exudation and after-film were also evaluated. The comparison of the invention is favorable.

TABLE IV

| Product | Cut Resistance | Stickiness | Resilience | Hardness | Exuding |
|---|---|---|---|---|---|
| Juicy Fruit | 5 | Yes | 5 | 8 | Moist, Not wet |
| Care-Free | 5 | Very | 5 | 6 | Moist, Not wet |
| Formula A Experiment 1-28-1 (XXIII) using SBR synthetic rubber gum | 5 | Slight | 5 | 5 | Moist, Not wet |

The water containing experimental gum composition contains 55% liquid, including glycerine, but still has the desirable typical chewing gum properties.

A natural gum base, e.g., gum chicle, is less preferred because it does not have the elastic properties of the SBR synthetic rubber gum base. In fact, SBR synthetic rubber gum base is the gum base used for bubble gum. Typical compsoitions of SBR rubber gum base are available from L. A. Dreyfus Company under the names LADCO and GRANDE and natural chicle is available under the name PELOJA. The plasticizer is preferably a vegetable oil, such as coconut oil. A natural product known as LAD Plasticizer is also available from L. A. Dreyfus Company which works well to soften the gum but is slightly sticky to dentures.

Abrasive inorganic mineral fillers, such as calcium pyrophosphate used in Formula A, have the advantage of imparting a degree of cleansing character. Dicalcium phosphate dihydrate, used in Table II, is a good source of calcium and phosphate ions as saliva replacement in the mouth. Titanium dioxide pigment gives a good opaque white color to the gum when used as a secondary pigment and is easily dispersed. Cellulose fibers are helpful if there is a need to maintain an integral gum wad in the mouth. Too high an inorganic mineral level of filler produces a crumbly gum. Glycerine is desirable to decrease evaporation and to improve moisture retention in the mouth. Too high a level of glycerine interferes with the emulsification step in preparation. Flavors, such as peppermint, spearmint, fruit or a medicinal taste such as methyl salicylate improve the taste and odor. Mold and fungus control agents are necessary because of the high liquid-sweetener concentration. A combination of methyl and propyl esters of p-hydroxylbenzoate at a 0.1% to 1.0% level appears to give good stability.

EXAMPLES 2 THROUGH 7

In Table V below there is shown the formulations of Examples 2 through 7 to illustrate the scope of the invention using SBR synthetic rubber gum base.

TABLE V

| INGREDIENT | #2 | #3 | #4 | #5 | #6 | #7 |
|---|---|---|---|---|---|---|
| Gum Base (LADCO, GRANDE, PELOJA) | 29.5 | 29.5 | #4 | 32.0 | 30.0 | 29.5 |
| Plasticizer (LAD) | 4.15 | 5.25 | 4.0 | 6.0 | 4.0 | 4.0 |
| Solution (Table III) | 54.1 | 53.0 | 53.0 | 48.0 | 52.3 | 53.0 |
| Xylitol | 5.0 | — | — | 5.5 | — | — |
| Sorbitol | — | 2.0 | — | — | 6.0 | — |
| Mannitol | — | 3.0 | — | — | — | — |
| Sucrose | — | — | 5.0 | — | — | 5.0 |
| Saccharine | — | — | — | — | 0.1 | — |
| Calcium Pyrophosphate | 5.0 | — | 5.0 | — | — | 5.0 |
| Dicalcium Phosphate Dihydrate | — | 5.0 | — | — | — | — |
| Cellulose Fibers | — | — | 4.5 | 4.5 | — | — |
| Emulsifier (Span 60) | 0.5 | 0.5 | 1.0 | 1.0 | 0.5 | 1.0 |
| Glycerine | 1.0 | 2.0 | 2.0 | 2.3 | 1.2 | 1.0 |
| Wintergreen | — | — | — | 0.7 | 0.7 | — |
| Peppermint | 0.5 | 0.5 | — | — | — | — |
| Methyl Salicylate | — | — | 1.0 | — | — | 1.0 |
| Methyl Hydroxybenzoate | 0.25 | 0.25 | 0.25 | — | — | 0.25 |
| Propyl | — | — | — | 1.0 | 0.7 | — |
| Fluoride Ion | 20ppm | 20ppm | — | 1000ppm | 2ppm | — |
| Cetyl Pyridinium Chloride | — | — | — | — | 0.5 | — |

In the above Table V each of the examples 2 through 7 are based upon synthetic chewing gum base, SBR rubber (styrene butabutadiene copolymer) furnished by L. A. Dreyfus Company under the tradename LADCO mixed by the procedure described in Example 1. However, each of these examples may use natural gum chicle as the chewing gum base in the same proportion as shown in each example. The natural gum chicle is hydrophobic in the same degree as the synthetic SBR rubber but is somewhat more variable since it is obtained from wild rubber trees in South America of the family Sapotaceae and species Palaquien. It is harvested as balata from the wild trees by a process similar to leaf digestion. The natural gum base, e.g., gum chicle, is available under the tradename PEJOLA from L. A. Dreyfus Company. Although coconut oil is used as a preferred plasticizer, other vegetable oils may be used, such as soya oil, safflower oil and the like.

Medicaments such as cetyl pyridinium chloride in Example 6 are added to the water phase. Examples of proportions are shown in Table V. Various other ingredients, such as fluoride, may be added as medicinal treatments, as shown in Examples 1, 3, 5 and 6. To add fluoride ions to decrease tooth decay, sodium fluoride, sodium monofluorophosphate or stannous fluoride are the preferred additives depending on fillers, since some fillers retain fluoride ions. The level of the fluoride ion added may be from 2 up to 1000 parts per million depending upon the frequency of use and the degree of professional control. Treatment for caries control, as in Example 1, may include coating agents, such as cephalin or n-dodecyl amine, to retard caries formation. This is particularly effective with xerostoma patients. The present gum is an ideal vehicle for longer time contact of medicinal treatment of the oral cavity and the digestive system as well as for many other medicaments for which ingestion is desired.

Example 2 is especially adapted for xerostoma patients. The xylitol is fairly sweet. Note that effective concentration is 1/10 that of a standard sugarless formulation.

Example 3 is a distinctly softer gum than Example 2 and is satisfactory even for a patient with sore mucosa. The composition is slightly sticky to dentures.

Example 4 is a gum suitable to replace salt loss by athletes and to produce a comfortable dampness under conditions in which saliva is lacking and higher salt concentrations may be used.

Example 5 uses cellulose fibers as organic filler which will not absorb certain medicaments which may be absorbed by inorganic fillers. It also uses a higher percentage of plasticizer to make it softer with less sticking to acrylic dentures but is coherent. This example is designed for use by patients who will not tolerate fluoride tray treatment but will use the high fluoride level in the gum, under the dentist's supervision, to resist rampant caries in remaining teeth.

Example 6 is designed to produce a gel structure in the hydrophilic emulsified phase which delays the expression during chewing of the liquid phase. In an in vitro chewing cycle, produced by alternate compression and release of a ball and socket, the liquid was expressed more uniformly and over a longer period of time.

Finally, Example 7 shows a composition which may be used to dispense a drug to the digestive system, for example the Salk typs polio vaccine. In this case the water solution would be designed to best stabilize and activate the drug. Buffers and stabilizers may be added.

Observations on Mixing Characteristics of Examples 1 through 7

Examples 1 and 3 emulsified during mixing in a very smooth manner and followed the general procedure of mixing at a temperature of slightly above 60° C.

Example 4 had the best mixing liquid phase, believed to be due to the presence of sucrose.

Example 2 illustrates a mixture which required heating to 65° C. in order to completely blend with the solution.

In contrast to Examples 1, 2, 3 and 4, which used SBR synthetic rubber gum base, Example 5 used natural gum chicle base and mixing was more difficult because of the stringiness of the gum chicle. Temperatures between 68° C. and 70° C. throughout the mixing cycle gave some improvement.

Example 6 illustrates the effect of composition with respect to cellulose fibers where two different gum bases were used, gum chicle and SBR synthetic rubber gum. The SBR synthetic rubber gum base produced excellent mixing. Gum chicle produced poorer mixing, again due to stringiness.

Example 7 illustrates an example which mixed well in the Hobart Blender at a temperature below 60° C. It mixed well at 55° C., again illustrating the benefits of sucrose.

Examples 4 and 7 are especially suitable for relief of "dry mouth" during athletic contests and also for dispensing medication where fluoride is not permitted.

Having thus disclosed the invention, I now claim:

1. A chewing gum emulsified liquid composition for maintaining and adding to the liquid content in the mouth to ameliorate xerostoma and add mineral salts and water comprising:

from 40 to 62 parts water containing dissolved mineral salts, including sodium, potassium, calcium and magnesium chlorides, and potassium phosphates at a concentration of from 1% to 3% of the water constituting the dispersed phase;

from about 25 to 35 parts hydrophobic chewing gum base selected from the class consisting of gum chicle and SBR synthetic rubber gum as the dispersed phase;

from 2 to 2000 parts per million fluoride ions based on sodium fluoride, stannous fluoride or sodium fluorophosphate;

from about 3 to 6 parts by weight of water soluble carbohydrate sweetener which is dissolved in the mineral salt water solution;

from 1% to 3% glycerine to augment the liquid phase;

an emulsifier in a concentration of 0.1% to 1.0%;

from about 4% to 5% of a finely divided filler selected from the class consisting of cellulose fibrous filler, CMC and calcium phosphate filler.

2. A composition as claimed in claim 1 wherein said finely divided filler is fibrous cellulose.

3. A composition as claimed in claim 1 including from 0.1% to 1.0% preservative selected from the class consisting of methyl and propyl hydroxybenzoate.

4. A composition as claimed in claim 1 including cetyl pyridinium chloride as an antiseptic agent in a concentration of from 0.1% to 1.0%.

5. A composition as claimed in claim 1 including cephalin in a concentration of from 0.1% to 1.0%.

6. A composition as claimed in claim 1 including a flavoring agent.

7. A composition as claimed in claim 1 wherein the mineral salt solution has a concentration of 0.5% mineral salts total in the water phase.

8. A composition as claimed in claim 1 wherein the mineral salt solution has a concentration of 1.5% mineral salts total in the water phase.

* * * * *